United States Patent [19]

Grigoryev

[11] Patent Number: 4,796,631
[45] Date of Patent: Jan. 10, 1989

[54] ELECTRICAL MUSCLE STIMULATOR FOR KNEE STABILIZATION

[76] Inventor: Leon M. Grigoryev, 14 Hunts Mill Rd., Clinton, N.J. 08809

[21] Appl. No.: 60,660

[22] Filed: Jun. 11, 1987

[51] Int. Cl.$^4$ .............................................. A61N 1/32
[52] U.S. Cl. .............................. 128/421; 128/423 W; 128/80 C; 128/80 G
[58] Field of Search ............... 128/419 R, 421, 420 A, 128/420 R, 423, 423 W, 80 G, 80 C, 80 F

[56] References Cited

U.S. PATENT DOCUMENTS

| | | | |
|---|---|---|---|
| 3,083,712 | 4/1963 | Keegan | 128/423 W |
| 4,005,296 | 1/1977 | Olson | 128/423 W |
| 4,711,242 | 8/1987 | Petrofsky | 128/414 R |

OTHER PUBLICATIONS

"Computer Synthesized Walking" Petrofsky et al.; J. of Neurol. & Ortho. Med. & Surg., 10/85, pp. 214-230.

Primary Examiner—Lee S. Cohen
Assistant Examiner—David Shay

[57] ABSTRACT

The present invention involves an electrical muscle stimulator for knee stabilization in a leg having inadequate neurological and muscular control to obtain normalization of locomotion and includes a power source, muscle stimulation electrodes, a control unit with manual on/off and with two control on/off switches. One of these switches is responsive to a heel ground contact determining means and the other to a knee angle determining means. Stimulation can only be effected when both the knees are in contact with some weight pressure and the knee angle measuring means shows the knees bent to or beyond a preset angle. As soon as one of these two conditions are not met, stimulation ceases.

18 Claims, 2 Drawing Sheets

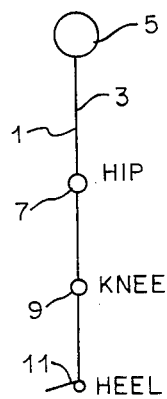
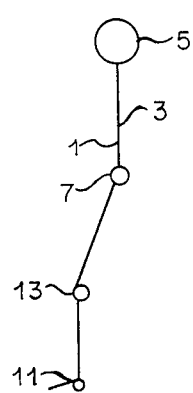
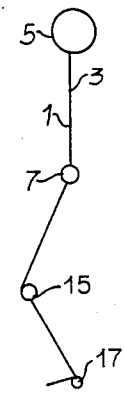
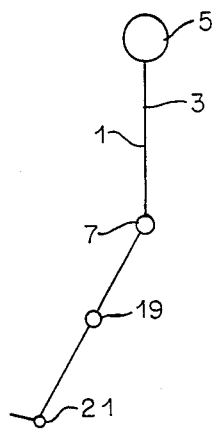
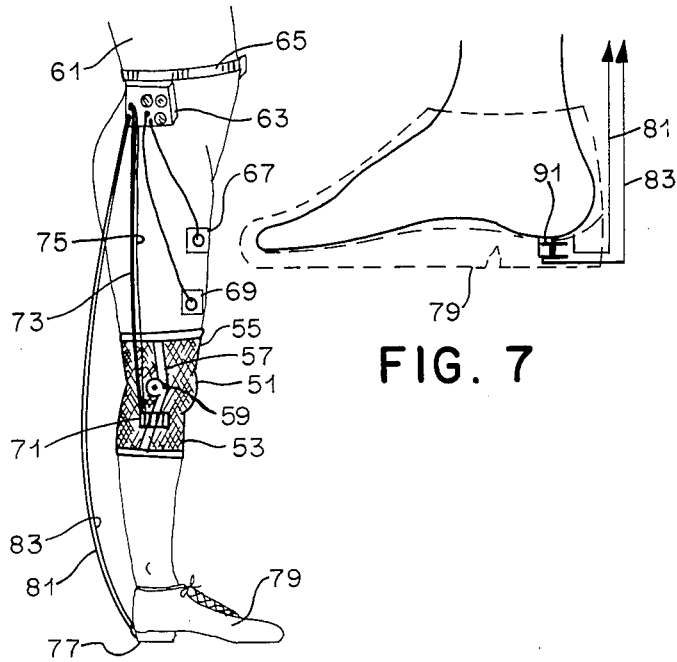
FIG. 2 — KNEE STRAIGHT; HEEL CONTACT (NO POWER)
FIG. 3 — KNEE BENT; HEEL CONTACT (POWER)
FIG. 4 — KNEE BENT; HEEL UP (NO POWER)
FIG. 5 — KNEE STRAIGHT; HEEL UP (NO POWER)
FIG. 6
FIG. 7

4,796,631

ELECTRICAL MUSCLE STIMULATOR FOR KNEE STABILIZATION

BACKGROUND OF THE INVENTION

1. Field of the Invention

The present invention is directed to electrical muscle stimulators and more particularly to such stimulators used to assist in stabilizing musculature of the knee in users having inadequate neurological and muscular control to obtain normal locomotion.

2. Prior Art Statement

It has been recognized for some years that electrical stimulation of a muscle can effectively cause muscular contraction or reaction which will aid to performing some bodily functions which could not have been otherwise achieved in patients and users having certain types of neurological and muscular deficiencies. Thus, devices have been developed to stimulate leg and arm muscles which provide electrical pulses in response to intelligently controlled or automatically controlled switches.

U.S. Pat. No. 2,737,183 issued to Charles Giaimo describes an electrical control device for partially denervated muscles. The device is a basic dry cell pack with electrical stimulation, through electrodes, to leg muscles. The user merely presses the switch when muscle stimulation is needed. The stimulation causes muscle reaction so as to effectuate leg movement in the forward direction to take a step. The manual switch may be automatic and be responsive to tilting, such as with a mercury switch.

U.S. Pat. Nos. 3,083,712 and 3,344,794 are both directed to devices for electrical stimulation of leg muscles wherein electrical pulses are activated in response to the closing of a circuit by a heel switch. In U.S. Pat. No. 3,083,712 to James Keegan, Jr., when pressure is placed on the heel, the switch is closed, a circuit is completed, current builds up in a capacitor and timely pulses are sent to muscles for stimulation via electrodes. In U.S. Pat. No. 3,344,794 to F. F. Offner et al, a similar system is shown except that pressure on the heel opens the circuit and pulse stimulation is interrupted. Thus, these two patents suggest opposite basis for pulse stimulation, i.e. heel on the ground and heel off the ground.

U.S. Pat. No. 3,083,712 to James Keegan, Jr. also describes alternative pulse control mechanisms such as a leg-strapped mercury switch which responds to a certain level of tilting, and the use of timing mechanisms to control sequential or spaced pulses to various electrode sites.

U.S. Pat. No. 4,005,296 to Robert Olson describes a specific disc switch for the heel for control of electrical muscle stimulation wherein the pulsing occurs only when the heel is off the ground. U.S. Pat. No. 3,881,496 to Jakob Vredenbregt et al acknowledges known heel control methods, and points out that when lifting the foot activated pulses are initiated but the heel switch exhibits deviations from natural locomotive patterns sometimes causing balance problems. This patent suggests that pressure changes at the ball of the foot be used as the parameter for initiating and ceasing pulsation.

Although not directed to the stimulation of muscles for locomotion by body part positions alone, U.S. Pat. No. Reissue 32,091 to David J. Stanton, is directed to a dual channel neuromuscular stimulator which involves complex computerization and wiring and either technician or second person operator control or heel switch stimulation.

U.S. Pat. No. 4,569,352 to Jerrold Petrofsky describes a very complex electrical and mechanical device for feedback control of movement for standing and for walking of paraplegics and quadriplegics. Complex electrical stimulation and control of hips, knees an ankles is described using external hip to knee metal rods, mechanical knee restriction supports and controlled angle and foot attachments. Various movable body mechanisms are locked and unlocked from position to position while muscle control with electrical pulse is employed. This device is extremely advanced and would likely be beyond the cost of most para- and quadriplegics and could not be strapped to or carried by the user.

Thus, the prior art is believed to establish that portable stimulators have been developed using different theories of when stimulation should occur and how controls should be applied to the body. Non-portable and complex computerized systems have been developed but may be beyond the reach of the typical person needing help and may be restricted by size, weight, complexity and the need for a qualified operator.

The present invention, on the other hand, represents a significant discovery in muscle stimulation for locomotive assistance by using simultaneous switches for both knee angle and heel contact to restrict the initiation, ceasation and timing of electrical pulse stimulation without the need for computerization or sophisticated, non-portable equipment.

SUMMARY OF THE INVENTION

The present invention involves an electrical muscle stimulator for knee stabilization in a leg having inadequate neurological and muscular control to obtain normalization of locomotion and includes a power source, muscle stimulation electrodes, a control unit with manual on/off and with two control on/off switches. One of these switches is responsive to a heel ground contact determining means and the other to a knee angle determining means. Stimulation can only be effected when both the heels are in contact with some weight pressure and the knee angle measuring means shows the knees bent to or beyond a preset angle. As soon as one of these two conditions are not met, stimulation ceases.

BRIEF DESCRIPTION OF THE DRAWINGS

The following drawings are presented, as follows:

FIG. 2 shows trunk, hip, knee and foot positions of a stick person in the basic standing position and indicates that the power to the electrode(s) of the present invention stimulator is not on;

FIG. 3 shows truck, hip, knee and foot positions of a stick person in a standing position when the knee is unstable and the power to the electrode(s) of the present invention stimulator is on;

FIG. 4 shows trunk, hip, knee and foot positions of a stick person in a basic walking position at the beginning of a stride wherein the power to the electrode(s) of the present invention stimulator is not on;

FIG. 5 shows trunk, hip, knee and foot positions of a stick person in a basic stand position at the end of a stride wherein which indicate whether the power to the electrode(s) of the present invention stimulator is not on;

FIG. 6 shows a side view of the lower portion of a body with the power and control pack, wiring, electrodes and switching means in place; and, FIG. 7 shows a cut side view of one heel ground contact determining means of the present invention.

DETAILED DESCRIPTION OF THE PRESENT INVENTION

Figure 1:
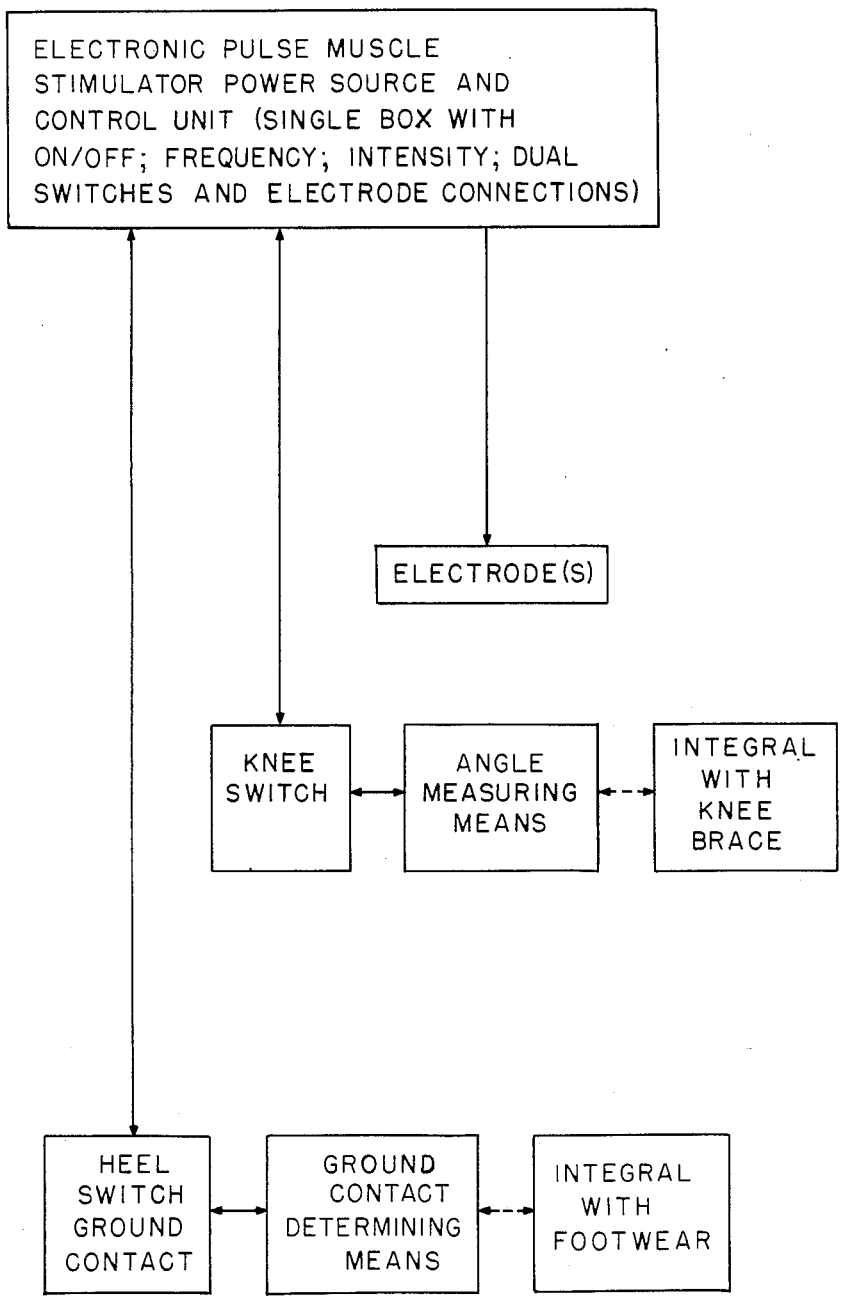
FIG. 1 shows a block diagram of the present invention in its preferred embodiments.

There are many individuals who suffer from various types of partial muscle incapacitation involving neurologically related disorders. Many suffer from temporary or permanent problems from injuries or disease which have a detrimental effect on the stabilizing musculature of the knee. These include patients with multiple sclerosis, diabetic neuropathy, lumbosacral radiculopathy, paraparesis, monoparesis secondary to spinal cord injury or disease, and other infirmities which cause falls or set backs due to knee malfunction (e.g. knee buckling) during locomotion.

Numerous devices have been developed to prevent such falls or to otherwise aid in normal ambulation. Many are mechanical; some are electrically operated mechanical devices. These tend to be bulky, unattractive and unnatural when functioning. Other devices involve electrical stimulation and have been reviewed above in the Prior Art Statement.

The present invention is directed to a unique, portable electrical muscle stimulator for knee stabilization to prevent buckling or other knee malfunction during attempted normal ambulation (locomotion) utilizing a combination of switches to more precisely control the timing and extent of stimulation during walking, without the need for computer aided timing and/or operation by a trained technician.

Thus, referring now more specifically to FIG. 1, the present invention stimulator is shown to be assembled in the following manner:

An electronic pulse muscle stimulator source and control unit is contained within a single container pack and is mountable or attachable to the belt or clothing of the user. The power source is a battery operated power source and functions in a manner similar to those described in the prior art, and those available commercially, except that the stimulating pulse can only occur when two switches are on instead of one switch. Thus, the device known as the Medtronic "Respond-11" (trademark of Medtronic, Inc., Minneapolis, Minn.) which is presently used for muscle stimulation may be wired to two switches in series to achieve the power source and control unit of the present invention. The pack is connected (by wires) to one or more electrodes through which the stimulation current is passed to the muscles. Thus, the electrode may be a strip electrode, a suction electrode, a strapped on electrode, an adhesive pad electrode, or any other type of muscle stimulation electrode known. Ideally, two electrodes are utilized and are placed in the area of the quadriceps.

The control unit may include frequency and intensity dials or these parameters may be preset by the physician or rehabilitation expert prescribing the device. The control unit has manual on/off means, e.g. push button, switch, touch pad or the like for turning the stimulator on and off. However, even when it is turned on, there will be no stimulating pulse to the electrode(s) until both the knee switch and the heel switch have been closed.

Thus, the control unit is connected by wiring or printed circuit to two on/off switches in series. One is the knee switch which closes when the knee angle measuring means reaches a preset minimum angle, and the other is the heel switch which closes when there is ground contact with sufficient weight pressure from the user at the ground contact determining means.

The knee angle measuring means may be a mercury switch or other liquid tilt switch, it may be magnetic or may be any other mechanism which is physically capable of closing a circuit in response to an angle change. Ideally, the knee angle measuring means would be a mechanical means, e.g. a device with an upper portion and a lower portion hingedly connected at the pivot point of the knee and attached to the side of the leg at the knee. When the angle between the upper portion and lower portion of the leg (above and below the knee pivot point) reaches a preset angle, the knee switch would close.

The knee angle measuring means of the present invention may be preset at some functional angle (which may vary from patient to patient) such as 5°, 7°, 10°, 12°, 15° or the like. In one preferred embodiment, the angle may be preset at an angle of at least 5°. In any event, once the present angle is reached, the switch would close to complete that portion of the circuit and remain closed as long as the measured angle was at or above the preset angle.

The heavy heel ground contact determining means may be generally of the design shown in the prior art, but with the circuit closing when the heel is down with weight atop it. Thus, the type shown in U.S. Pat. No. 3,083,712 to James E. Keegan, Jr. as shown in FIG. 2 and described in conjunction therewith may be used.

The knee switch and angle measuring means may optionally be an integral part of a brace and the heel switch and means may be an integral part of footwear such as a shoe, boot or sneaker.

Referring now to FIGS. 2 through 5, four positions of a walking "stick person" are shown. (Like parts in identical positions are identically numbered). Thus, stick person 1 is shown in the Figures, having trunk portion 3, head 5, hip 7 and the knee and heel numbered 9 and 11 in FIG. 2. As shown in FIG. 2, person 1 is standing and knee 9 is straight (0° angle) with heel 11 contacting the ground. Person 1 in this position shown in FIG. 2 with a present invention stimulator would have no power.

FIG. 3 shows person 1 with knee 13 bent (beyond a preset angle) and heel 11 contacting the ground. This combination of positions would result in stimulator power to the electrodes for the present invention wherein both the knee switch and the heel switch in series would be closed to complete the electric pulse circuit.

FIGS. 4 and 5 show person 1 with knee 15 more fully bent and heel 17 off the ground, and with knee 19 straight and heel 21 off the ground, respectively. In these positions, the present invention stimulator would not be activated.

The foregoing discussion and FIGS. 2 through 5 vividly illustrate the critical aspects of the functioning of the present invention. The following Table 1 shows a comparison of various prior art systems with the present invention and some pertinent conclusions:

TABLE 1

| STIMULATOR SYSTEM | POWER TO ELECTRODES | | | | OBSERVATIONS AND CONCLUSIONS |
| --- | --- | --- | --- | --- | --- |
| | KNEE STRAIGHT HEEL DOWN | KNEE BENT HEEL DOWN | KNEE BENT HEEL UP | KNEE STRAIGHT HEEL UP | |
| 1. Heel Contact Activation (Prior Art) | Yes | Yes | No | No | Activation for too long a period, and user cannot stand without shutting off system manually. Untimely muscle stimulation with shorter battery life. |
| 2. Heel Upactivation (Prior Art) | No | No | Yes | Yes | Same shortcomings as above. |
| 3. Mercury Switch-Leg Tilt (Prior Art) | No | Yes | Yes | No | Continuing pulse after musculature completed, counterproductive to straightening leg; excess battery usage. |
| 4. Computer Aided Stimulation (Prior Art) | Possible | Possible | Possible | Possible | Expense and operation overburdensome, some not possible. |
| 5. Heel Contact Plus Knee Angle Activation (Present Invention) | No | Yes | No | No | Proper stimulation at precise time without computer aid, overcoming all of above problems. |

As can be seen from Table 1, the present invention stimulator is the only system which gives stimulation at the needed instant when the knee is bending and the heel still has ground contact and is disengaged at all other times, yet is portable and simple to operate.

FIG. 6 shows a preferred embodiment of the present invention in use on the lower portion of person 61. Combination power source and control unit is shown as pack 63 which is attached to belt 65. Electrodes 67 and 69 are wired to pack 63 and are adhesively attached to the person 61 at the quadriceps area as shown. Knee 51 has a brace 55 with rigid member 57 and rigid member 53 being hingedly connected at pivot point 59. Attached to brace 55 is knee angle measuring means 71 which is wired to pack 63 with input and output wires 73 and 75. In this embodiment, means 71 has an upper portion which also acts as brace rigid member 57 and a lower portion which also acts as brace rigid member 53. Pivot point 59 includes an on/off switch which closes when the knee angle reaches a predetermined angle as determined by the angle between said upper portion and lower portion.

Referring now to both FIGS. 6 and 7, shoe 79 includes heel 77 which has input and output wires 81 and 83 connected to pack 63. Heel 77 contains heavy heel ground contact means 91 (in this case, bar spring plunger contact) wired as mentioned.

While one preferred stimulator of the present invention as described above has wiring for both the knee on/off switch and the heel on/off switch into the power pack and in-series wiring is arranged within the pack, an alternative embodiment would involve in-series wiring from one switch to the other with only one set of input/output wiring to the pack.

Obviously, numerous modifications and variations of the present invention are possible in light of the above teachings. It is therefore understood that within the scope of the appended claims, the invention may be practiced otherwise than as specifically described herein.

What is claimed is:

1. A portable electrical muscle stimulator for knee stabilization in a leg having inadequate neurological and muscular control to obtain normalization of locomotion, which comprises:

(a) a power source means for generating electrical current sufficient to stimulate muscle activation to the leg muscles;

(b) at least one muscle stimulation electrode for attachment to muscles of the leg, said electrode being connected to said power source means;

(c) a control unit for said power source means, having manual on/off means and having two control on/off switches which are activated and deactivated in response to predetermined conditions, a first switch of said two control on/off switches being responsive to knee angle and a second switch, of said two control on/off switches being responsive to heavy heel ground contact, said control unit being inactive unless said on/off means and both of said two control on/off switches are all activated;

(d) knee angle measuring means attachable to a knee and electrically connected to said first switch so as to activate said first switch when the knee angle is equal to or greater than a preset angle and to deactivate said first switch when the knee angle is less than said preset angle; and, (e) a heel ground contact determining means attachable to a heel of a foot and electrically connected to said second switch so as to activate said second switch when the heel has ground contact with adequate weight on the heel to establish standing, and to deactivate said second switch when the heel does not have ground contact with adequate weight on the heel to establish standing; said stimulator being capable of transmitting electrical pulses to quadriceps through said at least one electrode to simulate the quadriceps sufficiently to assist in the stabilizing musculature of the knee during locomotion.

2. The stimulator of claim 1 wherein a plurality of stimulation electrodes are connected to said power means source for attachment to quadriceps.

3. The stimulator of claim 1 wherein said power source is a power source operated by batteries and said control unit, power source and batteries are contained within a single container pack.

4. The stimulator of claim 3 wherein said container pack includes means for mounting said container pack on a belt or hip 5. The stimulator of claim 1 wherein said preset knee angle is at least 5°.

6. The stimulator of claim 1 wherein said heel ground contact determining means is a weight pressure sensitive vertical spring switch.

7. The stimulator of claim 6 wherein said heel ground contact determining means is located within a heel piece attachable to a heel of a foot.

8. The stimulator of claim 7 wherein said heel ground contact determining means is an integral part of an article of footwear.

9. The stimulator of claim 1 wherein said knee angle measuring means has an upper portion and a lower portion which are respectively adapted to be attached to the side of the leg above and below the bend of the knee and the knee angle measurement is mechanically determined by the angle between said upper portion and said lower portion of said means.

10. The stimulator of claim 1, wherein said knee angle measuring means in an integral part of a conventional knee brace.

11. The stimulator of claim 10 wherein a plurality of stimulation electrodes are connected to said power source means for attachment to quadriceps.

12. The stimulator of claim 10 wherein said power source is a power source operated by batteries said control unit, power source and batteries are contained within a single container pack.

13. The stimulator of claim 12 wherein said container pack includes means for mounting said container pack on a belt or hip 14. The stimulator of claim 10 wherein said preset knee angle is a least 5°.

15. The stimulator of claim 10 wherein said heel ground contact determining means is a weight pressure sensitive vertical spring switch.

16. The stimulator of claim 15 wherein said means is located within a heel piece attachable to a heel of a foot.

17. The stimulator of claim 16 wherein said means is an integral part of an article of footwear.

18. The stimulator of claim 10 wherein said knee angle measuring means has an upper portion and a lower portion which are respectively adapted to be attached to the side of the leg above and below the bend of the knee and the knee angle measurement is mechanically determined by the angle between said upper portion and said lower portion of said means.

* * * * *